United States Patent [19]

Ozaki et al.

[11] Patent Number: 5,091,549
[45] Date of Patent: Feb. 25, 1992

[54] SYNTHESIS OF D-MYOINOSITOL-1-PHOSPHATE

[75] Inventors: Shoichiro Ozaki; Takahiko Akiyama; Naoto Takechi, all of Matsuyama; Kunio Kageyama, Yokohama; Morihisa Machida, Kanagawa, all of Japan

[73] Assignee: The Yokohama Rubber Company, Ltd., Tokyo, Japan

[21] Appl. No.: 575,615

[22] Filed: Aug. 31, 1990

[30] Foreign Application Priority Data

Sep. 28, 1989 [JP] Japan .................................. 1-253679

[51] Int. Cl.$^5$ ................................................ C07F 9/117
[52] U.S. Cl. ........................................ 558/131; 558/194
[58] Field of Search ................................. 558/131, 155

[56] References Cited

U.S. PATENT DOCUMENTS 4,873,355 10/1989 Hobbs et al. ...................... 558/155

FOREIGN PATENT DOCUMENTS 0252227 1/1988 European Pat. Off.

OTHER PUBLICATIONS

M. J. Berridge et al., "Nature", vol. 306, Nov. 3, 1983, pp. 67-69.
M. J. Berridge et al., "Nature", vol. 312, Nov. 22, 1984, pp. 315-321.
S. Ozaki et al., "Tetahedron Lett.", vol. 27, No. 27, pp. 3157-3160 (1986).
D. A. Billington et al., "J. Chem. Soc., Chem. Commun", 1987, 314.
D. Mercier, "Tetrahedron", vol. 25, 1989, pp. 5681-5687.

Primary Examiner—Mary C. Lee
Assistant Examiner—Michael G. Ambrose
Attorney, Agent, or Firm—Finnegan, Henderson, Farabow, Garrett & Dunner

[57] ABSTRACT

A method of synthesizing D-myoinositol-1-phosphate from 1,2-($R^1$)-3-$R^2$-myoinositol compounds of the formula

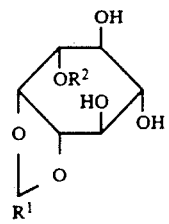

wherein $R^1$ is a bridging type protective group bonded to two oxygen atoms at the 1- and 2-position, and $R^2$ is a protective group coupled to the oxygen atom at the 3-position. D-Myoinositol-1-phosphate is useful as an intermediate for the production of inositol-1,4,5-triphosphate.

6 Claims, 1 Drawing Sheet

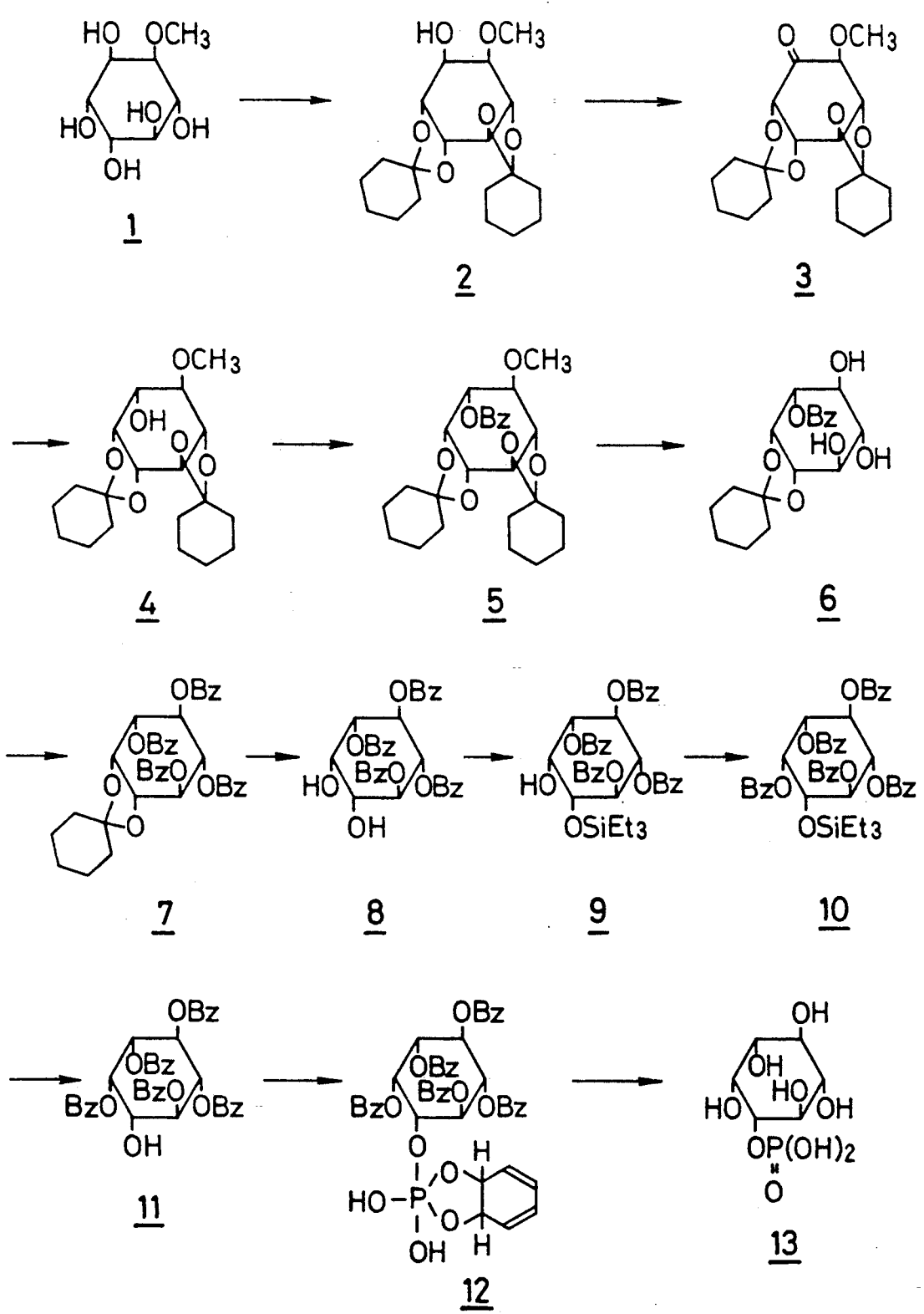

SYNTHESIS OF D-MYOINOSITOL-1-PHOSPHATE

BACKGROUND OF THE INVENTION

1. Field of the Invention

This invention is directed to a method of the synthesis of D-myoinositol-1-phosphate commonly accepted as a metabolic intermediate for inositol-1,4,5-triphosphate.

2. Description of the Prior Art

Inositol-1,4,5-triphosphate has of late enjoyed credit as a second messenger of information in a cellular system of human beings. This has led to extensive research on the physiological activity and mechanism of and the pharmaceutical effect of inositol-1,4,5-triphosphate and its metabolites.

Inositol-1,4,5-triphosphate is restrictedly available from organisms as it is less isolable in pure form on hydrolysis and extraction and rather existent in only appreciable content. Many attempts have been made to cope with this problem to obtain such inositol triphosphate via chemical synthesis as taught by M. J. Berridge et al., Nature 306, 67 (1983) and ibid., 312, 315 (1984). In 1985 inositol-1,4,5-triphosphate was successfully synthesized from myoinositols by S. Ozaki, one of the present inventors, and his colleagues as reported by S. Ozaki et al., Terahedron Lett., 27, 3157 (1986).

Myoinositols useful as the starting materials are liable to necessarily form equimolar enantiomers in the course of synthesis. This is due to the myoinositols being of a meso type in nature. To obtain inositol-1,4,5-triphosphate of optical activity, a given myoinositol is required to be optically resolved, for example, by a method in which a racemate is reacted with an optically active compound to synthesize a diastereomer, followed by separation of the same as on column chromatography, or by a method in which a racemic compound is separated with use of a suitable column. Optical resolution, however, has a drawback in that it tends to invite decreased product yield and reduced operation efficiency.

It has also been proposed that inositols of optical activity be synthesized with use of optically active starting material, hence without resort to optical resolution, as disclosed by S. Ozaki et al., J. Org. Syn. Chem., Japan, 47, 363 (1989). This prior mode of synthesis has been found too tedious in operation and too low in yield to warrant commercial application.

A keen demand has been voiced, though quite recently, for chemical syntheses of inositol-1,4,5-triphosphate and its metabolites. In addition to inositol-1,4,5-triphosphate, certain other inositol phosphates have been synthetically obtained in which are included inositol-2,4,5-triphosphate, inositol-1,3,4,5-tetraphosphate and inositol-1,3,4-triphosphate, the latter two compounds being regarded as metabolic products for inositol-1,4,5-triphosphate.

D-Myoinositol-1-phosphate is accepted in the art as a metabolic intermediate for inositol-1,4,5-triphosphate and as a physiologically active material. However, insufficient availability leaves much unsolved with respect to the effect of the intermediate. The only one method known to synthesize D-myoinositol-1-phosphate is disclosed by the Merch group, D. A. Billington et al., J. Chem. Soc., Chem. Commun., 314 (1987). The Merch method involves the use of optical resolution, leading to the foregoing difficulties.

Myoinositol-1-phosphate of an L type can be synthesized from L-quebrachitol as reported by S. D. Gero, Tetrahedron Lett., 25, 5681–5687 (1989).

SUMMARY OF THE INVENTION

The present invention seeks to provide a new method of synthesizing D-myoinositol-1-phosphate with utmost efficiency of operation and high yield of product without involving objectionable optical resolution.

D-Myoinositol-1-phosphate according to the invention, a D-type metabolic intermediate for inositol-1,4,5-triphosphate, is commonly expected to have physiological activity. The intermediate is applicable as a reagent or physiologically active material for use in biochemistry in particular.

Many other objects and advantages of the invention will become readily understood from the following description upon reading in conjunction with the accompanying drawing.

More specifically, the invention provides a method of the synthesis of D-myoinositol-1-phosphate from 1,2-($R^1$)-3-$R^2$-myoinositol as a starting material of the formula

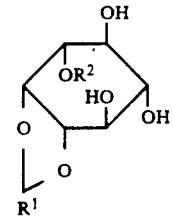

where $R^1$ is a protective group of a bridging type bonded to two oxygen atoms at the 1- and 2-position, and $R^2$ is a protective group coupled to an oxygen atom at the 3-position, which method comprises the steps of (a) protecting the starting material with a protective group at hydroxyl groups at the 4-, 5- and 6-position, (b) removing from compound (a) a protective group bonded to two oxygen atoms at 1- and 2-position, thereby replacing two hydroxyl groups at the two positions, (c) triethylsilylating compound (b) at the hydroxyl group at the 1-position, (d) protecting compound (c) with a protective group at the hydroxyl group at the 2-position, (e) regenerating a hydroxyl group into compound (d) at the 1-position by reaction with a Lewis acid, (f) phosphate-esterifying compound (e) at the 1-position by reaction with 1,5-dihydro-3-diethylamino2,4,3-benzodioxaphosphepin, and (g) reducing compound (f).

BRIEF DESCRIPTION OF THE DRAWING

The accompanying drawing is a schematic representation of the sequence of reactions embodying the present invention and ranging from L-quebrachitol to D-myoinositol-1-phosphate via 1,2-(cyclohexylidene)-3-benzoyl myoinositol.

DETAILED DESCRIPTION OF THE INVENTION

Starting materials eligible for purposes of the present invention are 1,2-($R^1$)-3-$R^2$-myoinositol compounds of the formula

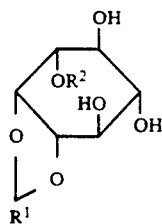

where $R^1$ is a protective group of a bridging type bonded to two oxygen atoms at the 1- and 2-position, and $R^2$ is a protective group coupled to an oxygen atom at the 3-position.

Specific examples of the $R^1$ substituent include cyclohexylidene, —$CH_2COCH_2$— groups and the like. The $R^2$ substituent may suitably be chosen for example from benzoyl or benzyl groups and the like.

No particular limitation is imposed upon the source of supply of 1,2-($R^1$)-3-$R^2$-myoinositol which, however, is conveniently induced from L-quebrachitols. Particularly preferred is an L-quebrachitol in which a hydroxyl group at the 1-position is inversed and protected, followed by demethylation of a methoxy group at the 2-position.

A preferred embodiment of synthesizing 1,2-($R^1$)-3-$R^2$-myoinositol from an L-quebrachitol will be described in conjunction with the drawing representation.

L-Quebrachitol 1 has at the 2-position a methoxy group resulting from methyl etherification and at the 3- and 4-position and at the 5- and 6-position two neighboring pairs of hydroxyl groups. These hydroxyl groups may selectively be protected by the use of a bridging type protective group or groups in which are included examples of cyclohexanone, acetone and the like. The protective group may be introduced in the form of an enol ether for instance as 1-ethoxycyclohexene in the case of cyclohexanone or as 2,2-dimethoxypropane in the case of acetone.

L-Quebrachitol 1 is protected with a protective group specified above, with cyclohexanone in the drawing, thereby forming compound 2. In anhydrous benzene and acid anhydride compound 2 is oxidized with dimethyl sulfoxide into compound 3 in which a hydroxyl group at the 1-position is selectively oxidized to form a ketone. Compound 3 is converted into compound 4 via oxidation and reduction at $-78°$ C. with lithium borohydride, compound 4 being then benzoylated with benzoyl halide into compound 5. By reaction with aluminum halide and sodium iodide compound 5 is subjected to demethylation and removal of the protective group at the 3-and 4-position. There is obtained 1,2-(cyclohexylidene)-3-benzoyl myoinositol as compound 6.

To protect the 1-, 2- and 3-position, any other protective groups may be employed, where desired, in place of cyclohexanone and acetone.

L-Quebrachitol, i.e. L-(—)-2-0-methyl-chiro-inositol, is a monomethyl ether of an inositol which is by itself optically active. This type of compound permits the formation of 1,2-(R1)-3-R2-myoinositol without need for optical resolution.

L-Quebrachitol is widely distributed in quebraco barks, latices of Hevea brasiliensis and various other plants. Japanese Patent Laid-Open Publication No. H02-19332 discloses collecting L-quebrachitol from serums resulting from treatment of natural rubber latices.

D-Myoinositol-1-phosphate may be obtained from 1,2-(R1)-3-R2-myoinositol, in the practice of the invention, by the reaction sequence shown in the drawing. In such instance 1,2-(R1)-3-R2-myoinositol is exemplified to be 1,2-(cyclohexylidene)-3-benzoyl myoinositol.

The method according to the invention is made up essentially of seven steps to be mentioned.

A first step serves to protect 1,2(R1)-3-R2-myoinositol at hydroxyl groups at the 4-, 5- and 6-position. A protective group is introduced to prevent the highly reactive hydroxyl groups against chemical change in subsequent steps. Protective groups are not specifically restrictive except for a triethylsilyl group to be used in a subsequent step, but they may be preferably of a type having a behavior similar to that of a protective group bonded to an oxygen atom at the 3-position. In compound 6 seen in the drawing, i.e. 1,2-(cyclohexylidene)-3-benzoyl myoinositol, a benzoyl or benzyl group is situated at the 3-position. A benzoyl or benzyl group is preferred to be introduced also at the 4-, 5- and 6-position. Compound 6 is reacted for example with triethylamine and benzoyl halide so that a benzoyl group is introduced at the 4-, 5- and 6-position, whereby compound 7 is provided.

A second step is adapted to remove from compound 6 the protective group bonded to two oxygen atoms at the 1- and 2-position or otherwise used to concurrently protect two hydroxyl groups at both positions. Removal of that protective group attaches hydroxyl groups to the 1- and 2-position. The second step may be effected in conventional manner with use of any known compounds and reaction conditions which may of course be varied with the nature of bridging type protective groups used. Compound 7 is configured to have at the 1- and 2-position two oxygen atoms coupled with a cyclohexylidene protective group of a bridging type. Compound 7 is reacted for example with a trifluoroacetate-methanol mixture so that the cyclohexylidene group is removed to bond hydroxyl groups to the 1- and 2-position, thereby giving compound 8.

A third step involves protecting compound 8 at the hydroxyl group at the 1-position via triethylsilylation. This position should importantly be phosphatized in a final step. Regeneration of that hydroxyl group is necessary only at the 1-position prior to arrival at the final step. A unique protective group is useful at the 1-position which is different in behavior from one at other positions and also easy in removal. Due to the presence of two hydroxyl groups at the 1- and 2-position upon completion of the second step, the third step should use a protective group having the ability to selectively introduce into the 1-position. Chosen to this end is a triethylsilyl group. Compound 8 when reacted with triethylsilyl halide is selectively triethylsilylated at the 1-position into compound 9.

A fourth step is set to protect the hydroxyl group of compound 9 at the 2-position. A protective group suitable for use at this position may be other than the triethylsilyl group and is conveniently similar in behavior to that at the 3-, 4-, 5- and 6-position. A benzyl or benzoyl group is preferred because compound 9 is incorporated with a benzoyl group at the 3- to 6-position. Compound 9 is protected with a benzoyl group at each of these four positions by reaction with triethylamine and benzoyl halide, whereby compound 10 is provided.

A fifth step is intended to regenerate a hydroxyl group in compound 10 at the 1-position. To this position regeneration should solely be limited in the fifth step. As a reactant a Lewis acid is suitable which is incapable of scission of oxygen-carbon linkage, but not of oxygen-silicon linkage. Lewis acids may be selected for example from p-toluene sulfonate, aluminum trichloride, boron trifluoride, phosphoric acid, sulfur trioxide, zinc dichloride, tin tetrachloride, sulfuric acid and the like among which p-toluene sulfonate is particularly preferred. Compound 10 is reacted with 80% acetic acid and p-toluene sulfonate to thereby remove the protective group and to regenerate a hydroxyl group at the 1-position alone. Compound 11 is thus provided.

A sixth step is contemplated to phosphate-esterify compound 11 at the hydroxyl group at the 1-position. This reaction may be carried out in the presence of a 1,5-dihydro-3-diethylamino-2,4,3-benzodioxaphosphepin compound represented by the formula

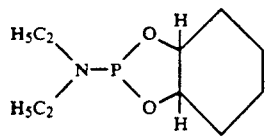

More specifically, scission of the N-P linkage in that compound allows the phosphorus atom to be attached to compound 11 at an oxygen atom located at the 1-position. In this state the phosphorus atom is trivalent which should be made pentavalent with two hydroxyl groups incorporated via a reaction with m-chloroperbenzoate as one example of an oxidizing agent and water. Compound 11 is reacted with 1,5-dihydro-3-diethylamino-2,4,3-benzodioxaphosphepin, followed by oxidation, into compound 12.

A seventh step is directed to reducing compound 12, whereby it is structured to have a phosphate group converted at the 1-position and hydroxyl groups regenerated at the 2-, 3-, 4-, 5- and 6-position. Put to use are reducing agents of high reactivity such as sodium hydride and the like. A palladium-based catalyst may preferably be employed for the reduction reaction. Compound 12 is reduced with sodium hydride into compound 13 or D-myoinositol-1-phosphate according to the invention.

Where it is found necessary, extraction, purification and other treatments may be performed in each of the above specified steps.

The following examples are given to further illustrate the invention.

EXAMPLE 1 synthesis of 1,2-(cyclohexylidene)-3-benzoyl myoinositol from L-quebrachitol a) To L-quebrachitol 1 (3.00 g, 15.4 mmol) were added in nitrogen atmosphere anhydrous dimethylformamide (5 ml) and then with cooling at 0° C. ethoxycyclohexene (6.60 ml, 46.3 mmol) and p-toluene sulfonate (0.294 g, 1.54 mmol). Heating was done at 80° C. Two separate portions of ethoxycyclohexene were further added with a first amount (2.20 ml, 15.4 mmol) after 1.5 hours and with a second amount (1.10 ml, 7.72 mmol) after lapse of 1.5 hours. The whole mixture was stirred for 0.5 hour after lapse of another which the reaction liquid was poured into an ice-containing separatory funnel and incorporated with saturated sodium hydrogencarbonate solution. Upon dichloromethane extraction the resulting organic layer was washed twice with saturated sodium hydrogencarbonate solution and once with water, followed by drying with sodium sulfate anhydride and by subsequent filtration. From the filtrate the solvent was removed by vacuum distillation. By column chromatography (ethyl acetate/hexane=2/1) and also by recrystallization with hexane the residue was purified to give compound 2.

yield: 4.01 g (73%)
Rf: 0.33 (ethyl acetate/hexane=$\frac{1}{2}$)
mp: 114.5°-115.5° C.
$[\alpha]_D^{20}$: $-15.5°$ (c, 3.50 in CHCl$_3$)
$^1$H-NMR ($\delta$ in CDCl$_3$, 270 MHz): 1.35-1.75 (20H, m); 2.80 (1H, s); 3.57 (3H, s); 3.54-3.75 (3H, m); 426-4.39 (3H, m)
IR (nujol): 3500, 1100, 1035 cm$^{-1}$
elementary analysis as C$_{19}$H$_{30}$O$_6$ (%): C: 64.39, H: 8.53 (calculated); C: 64.38, H: 8.67 (found)
* mp: 117°-119° C.
* $[\alpha]_D^{20}$: $-19.3°$ (c, 0.775 in CHCl$_3$)
* data taught by S. D. Gero, Tetrahedron Lett., 25, 5681-5687 (1969).

b) To compound 2 (1.00 g, 2.82 mmol) were added in nitrogen atmosphere anhydrous benzene (18 ml) and then at room temperature dimethyl sulfoxide (2.00 ml, 28.2 mmol) and anhydrous acetic acid (1.33 ml, 14.1 mmol). Refluxing was effected with heat for 7 hours. In an ice-containing separatory funnel the reaction liquid was washed once with water and once with saturated sodium hydrogencarbonate solution. Sodium sulfate anhydride was added to dry the resulting organic layer which was thereafter filtered, the filtrate being vacuum-distilled to remove the solvent. The residue was column-chromatographed (ethyl acetate/hexane=$\frac{1}{2}$) to give compound 3.

yield: 0.99 g (100%)
Rf: 0.45 (ethyl acetate/hexane=1/3)
$[\alpha]_D^{22}$: $-12.0°$ (c, 7.07 in CHCl$_3$)
$^1$H-NMR ($\delta$ in CDCl$_4$, 90 MHz): 1.30-1.87 (20H, m); 3.47 (3H, s); 3.24-3.70 (2H, m); 3.73-3.93 (1H, m); 4.36-4.71 (2H, m);
IR (nujol): 1730, 1220, 1160, 1090 cm$^{-1}$ c) To compound 3 (1.692 g, 4.801 mmol) were added in nitrogen atmosphere anhydrous tetrahydrofuran (40 ml) and then at $-78°$ C. lithum borohydride (0.105 g, 4.801 mmol). Stirring was done for 30 minutes. In an ice water-containing separatory funnel the reaction liquid was extracted with diethyl ether. The resulting organic layer after being washed once with water was dried with sodium sulfate anhydride, followed by filtration and evaporation in vacuo. The residue was column-chromatographed (ethyl acetate/hexane=$\frac{1}{2}$) after which compound 4 was provided.

yield: 1.560 g (92%)
Rf: 0.34 (ethyl acetate/hexane=3/1)
$[\alpha]_D^{20}$: $-3.9°$ (c, 6.62 in CHCl$_3$)
$^1$H-NMR ($\delta$ in CCl$_4$, 90 MHz): 1.17-1.90 (20H, m); 2.12-2.40 (1H, br); 3.40 (3H, s); 3.14-3.73 (2H, br); 3.82 (1H, br. s); 3.97-4.40 (3H, m)
IR (nujol): 3570, 1160, 1100, 1040 cm$^{-1}$ d) To compound 4 (1.560 g, 4.40 mmol) were added in nitrogen atmosphere anhydrous dichloromethane (15 ml) and then at 0° C. triethylamine (0.797 ml, 5.72 mmol), benzoyl chloride (0.613 ml, 5.28 mmol) and dimethylamino pyridine (in a catalytically effective amount). The mixture was stirred overnight at room temperature. In a separatory funnel the reaction liquid was washed once with saturated sodium chloride solution and once with water. Sodium sulfate anhydride was added to dry the resulting organic layer which was thereafter filtered, the filtrate being distilled in vacuo. By column chromatography (ethyl acetate/hexane=1/10) the residue was purified to give compound 5.

yield: 1.623 g (80%)
Rf: 0.55 (ethyl acetate/hexane=1/3)
$[\alpha]_D^{22}$: $-5.1°$ (c, 2.43 in CHCl$_3$)
$^1$H-NMR ($\delta$ in CCl$_4$, 90 MHz): 1.15–1.80 (20H, m); 3.53 (3H, s); 3.29–3.52 (1H, br); 3.83–4.21 (2H, br. m); 4.22–4.53 (2H, m); 5.24–5.35 (1H, br); 7.35–7.58 (3H, m); 7.95–8.15 (2H, m)
IR (neat): 1705, 1255, 1100, 700 cm$^{-1}$ e) To compound 5 (1.250 g, 2.73 mmol) were added in nitrogen atmosphere anhydrous acetonitrile (30 ml) and then at 0° C. aluminum chloride (3.63 g, 27.3 mmol) and sodium iodide (4.09 g, 27.3 mmol). Several minutes later the mixture was elevated at room temperature and stirred for 12 hours. Dichloromethane extraction was performed of the reaction liquid in a separatory funnel filled with ice water. The resulting organic layer was washed with saturated sodium chloride solution, saturated sodium thiosulfate solution and water each once in that order. Drying was done with sodium sulfate anhydride, followed by filtration and by evaporation of the solvent. By thin layer chromatography (ethyl acetate/hexane=10/1 and dichloromethane/methanol=10/1) the residue was purified to obtain compound 6, i.e. 1,2-(cyclohexylidene)-3-benzoyl myoinositol.

yield: 0.827 g (83%)
Rf: 0.25 (ethyl acetate/hexane=3/1)
$[\alpha]_D^{22}$: $+53.3°$ C. (c, 1.22 in EtOH)
$^1$H-NMR ($\delta$ in CDCl$_{3+DMSO-d_6}$, 90 MHz): 1.14–1.90 (10H, m); 2.70 (3H, br); 3.20–4.70 (5H, br. m); 5.12–5.34 (1H, br); 7.30–7.68 (3H, m); 8.03–8.23 (2H, m)
IR (nujol): 3490, 1700, 1275, 1105, 700 cm$^{-1}$

EXAMPLE 2 synthesis of D-myoinositol-1-phosphate from 1,2-(cyclohexylidene)-3-benzoyl myoinositol a) To compound 6 (81.0 mg, 0.222 mmol) were added in nitrogen atmosphere anhydrous dichloromethane (3 ml) and then at 0° C. triethylamine (0.149 ml, 1.7 mmol), benzoyl chloride (0.116 ml, 0.999 mmol) and dimethylamino pyridine (in a catalytically effective amount). Stirring was done for 3 hours at room temperature. On transfer of the reaction liquid to a separatory funnel the resulting organic layer was washed once with 0.5N hydrochloric acid and once with saturated sodium hydrogencarbonate solution. Drying was carried out with sodium sulfate anhydride, followed by filtration, the filtrate being distilled in vacuo. The resultant oily material was purified by column chromatography (dichloromethane/hexane=3/1), whereby compound 7 was provided.

yield: 148.3 mg (99%)
Rf: 0.55 (dichloromethane/hexane=$\frac{1}{3}$)
$[\alpha]_D^{26}$: $+29.3°$ (c, 3.00 in CHCl$_3$)
$^1$H-NMR ($\delta$ in CCl$_{4+CDCl_3}$, 90 MHz): 1.12–1.96 (10H, m); 4.50 (1H, t, J=6.0 Hz); 4.80 (1H, t, J=5.1 Hz); 5.57–5.97 (3H, m); 6.13 (1H, t, J=9.0 Hz); 7.00–7.53 (12H, m); 7.67–8.13 (8H, m)
IR (nujol): 1700, 1250, 1080, 1050, 680 cm$^{-1}$ b) To compound 7 (115.8 mg, 0.171 mmol) was added a mixture of trifluoroacetate and methanol (8:1, 6 ml). The whole mixture was stirred for 10 minutes at room temperature. After solvent evaporation the residue was purified by thin layer chromatography (ethyl acetate/hexane = $\frac{1}{3}$). Compound 8 was provided.

yield: 95.2 mg (93%)
Rf: 0.15 (ethyl acetate/hexane=$\frac{1}{3}$)
$[\alpha]_D^{26}$: $+22.9°$ (c, 1.40 in CHCl$_3$)
$^1$H-NMR ($\delta$ in CDCl$_3$, 90 MHz): 3.53–4.20 (3H, br); 4.56 (1H, br. s); 5.42 (1H, dd, J$_{34}$=9.9 Hz, J$_{32}$=2.4 Hz); 5.67–6.10 (2H, m); 6.33 (1H, t, J=9.0 Hz); 7.00–7.50 (12H, m); 7.55–8.06 (8H, m)
IR (nujol): 3450, 1710, 1260, 1100, 700 cm$^{-1}$ c) To compound 8 (74.2 mg, 0.124 mmol) were added in nitrogen atmosphere anhydrous pyridine (1 ml) and then at 0° C. triethylsilyl chloride (0.0313 ml, 0.186 mmol). The mixture was stirred for 2 hours at room temperature. In an ice-containing separatory funnel the reaction liquid was extracted with dichloromethane. The resulting organic layer was washed once with saturated potassium hydrogensulfate solution, followed by drying with sodium sulfate anhydride and by subsequent filtration. The filtrate was evaporated in vacuo. The resultant oily material was column-chromatographed (ethyl acetate/hexane=$\frac{1}{3}$) to give compound 9.

yield: 88.5 mg (100%)
Rf: 0.45 (ethyl acetate/hexane=$\frac{1}{3}$)
$[\alpha]_D^{26}$: $+22.4°$ (c, 1.43 in CHCl$_3$)
$^1$H-NMR ($\delta$ in CDCl$_3$, 90 MHz): 0.37–1.00 (15H, m); 2.96 (1H, s); 4.22 (1H, dd, J$_{12}$=3.0 Hz, J$_{16}$=9.0 Hz); 4.43 (1H, t, J$_{21}$=J$_{23}$=3.0 Hz); 5.46 (1H, dd, J$_{32}$=3.0 Hz, J$_{34}$=9.9 Hz); 5.62–6.13 (2H, m); 6.33 (1H, t, J=9.0 Hz); 7.03–7.52 (12H, m); 7.64–8.10 (8H, m)
IR (nujol): 3450, 1710, 1260, 1090, 700 cm$^{-1}$ d) To compound 9 (85.0 mg, 0.120 mmol) were added in nitrogen atmosphere anhydrous dichloromethane (1.5 ml) and then at 0° C. triethylamine (0.0333 ml, 0.240 mmol), benzoyl chloride (0.0278 ml, 0.240 mmol) and dimethylamino pyridine (in a catalytically effective mount) The mixture stirred for 2 hours at room temperature. Dichloromethane extraction of the reaction liquid was done in a separatory funnel. The resulting organic layer was washed once with saturated potassium hydrogensulfate solution and thereafter dried with sodium sulfate anhydride. After filtration the solvent was removed by vacuum distillation. By column chromatography (ethyl acetate/hexane=$\frac{1}{3}$) the resultant oily material was purified to give compound 10.

yield: 81.4 mg (84%)
Rf: 0.50 (ethyl acetate/hexane=$\frac{1}{3}$)
$[\alpha]_D^{26}$: $+55.9°$ (c, 1.11 in CHCl$_3$)
$^1$H-NMR ($\delta$ in CDCl$_3$, 90 MHz): 0.37–0.97 (15H, m); 4.40 (1H, dd, J$_{12}$=3.0 Hz, J$_{16}$=9.0 Hz); 5.63 (1H, dd, J$_{32}$=3.0 Hz, J$_{34}$=10.2 Hz); 5.75–6.38 (4H, m); 7.10–7.68 (15H, m); 7.70–8.25 (10H, m)
IR (nujol): 1710, 1250, 1090, 700 cm$^{-1}$ e) Compound 10 (73.0 mg, 0.0896 mmol) was dissolved in chloroform (in a small amount), followed by addition of acetic acid (1 ml) and p-toluene sulfonate (25.6 mg, 0.134 mmol). The whole mixture was stirred for one hour at room temperature. The reaction liquid was extracted with dichloromethane in a separatory funnel. Washing of the resulting organic layer was done once with water and once with saturated potassium hydrogensulfate solution. Sodium sulfate anhydride was added to dry the organic layer which was then filtered and evaporated in vacuo. The resultant oily material was column-chromatographed (ethyl acetate/hexane=1/1) to provide compound 11.

yield: 62.8 mg (100%)

Rf: 0.20 (ethyl acetate/hexane = $\frac{1}{1}$)
$[\alpha]_D^{26}$: +65.2° (c, 1.15 in CHCl$_3$)
$^1$H-NMR ($\delta$ in CDCl$_3$, 90 MHz): 2.80-3.15 (1H, br); 4.26-4.60 (1H, br); 5.62 (1H, dd, J$_{32}$=3.0 Hz, J$_{34}$=10.2 Hz); 5.83-6.42 (4H, m); 7.09-7.66 (15H, m); 7.70-8.30 (10H, m)
IR (nujol): 3450, 1710, 1260, 1080, 700 cm$^{-1}$ f) To compound 11 (51.8 mg, 0.0739 mmol) were added in nitrogen atmosphere anhydrous dichloromethane (1.5 ml) and 1H-tetrozole (8.8 mg, 0.12 mmol). The mixture was stirred at room temperature, followed by addition of 1,5-dihydro-3-diethylamino-2,4,3-benzodioxaphosphepin (26.5 mg, 0.111 mmol). Stirring was continued for 10 minutes at room temperature. On pouring of distilled water (0.0265 ml, 1.48 mmol) the whole mixture was stirred for 10 minutes at room temperature and thereafter incorporated with cooling at −40° C. with m-chloroperbenzoate (25.5 mg, 0.148 mmol). After temperature rise at room temperature stirring was further continued for 10 minutes. The reaction liquid was extracted with dichloromethane in a separatory funnel. Washing of the resulting organic layer was done once with 10% sodium sulfite solution and once with saturated sodium hydrogencarbonate solution. Sodium sulfate anhydride was added to dry the organic layer which was thereafter subjected to filtration and vacuum evaporation. By thin layer chromatography (ethyl acetate/hexane=1/1) the resultant oily material was purified to give compound 12.

yield: 55.6 mg (85%)
Rf: 0.45 (ethyl acetate/hexane=1/1)
$[\alpha]_D^{26}$: +22.7° (c, 1.19 in CHCl$_3$)
$^1$H-NMR ($\delta$ in CDCl$_4$, 90 MHz): 4.67 (2H, d, J=27 Hz); 4.84 (2H, d, J=27 Hz); 5.14-6.37 (6H, m); 6.71-8.20 (29H, m)
IR (nujol): 1710, 1240, 1080, 1000, 700 cm$^{-1}$ g) To compound 12 (46.0 mg, 0.0521 mmol) were added methanol (1 ml) and chloroform (in a small amount) and then 10% palladium carbon (in one spatula). After hydrogen replacement the mixture was stirred for 4 hours at room temperature. Upon filtration of palladium carbon the filtrate was concentrated and dried. To the residue were added methanol (1 ml) and then at 0° C. sodium hydride (37.5 mg, 1.56 mmol). Stirring was done overnight at room temperature. The reaction liquid after being taken into a separatory funnel was extracted with addition of dichloromethane and distilled water. The resulting aqueous layer was allowed to pass through cationic ion exchange resin (Dia Ion, SKIB, HT type) and then washed with ether. Cyclohexylamine (0.1 ml) was added to the aqueous layer which was subsequently vacuum-distilled to remove the solvent and dried to give a crystalline material. Recrystallization with a water-acetone mixture produced compound 13, i.e. D-myoinositol-1-phosphate according to the invention.

yield: 22.5 mg (94%)
Rf: 0.2 (n-propanol/aq. ammonia/ water=5/4/1)
mp: 191°-193° C.
$[\alpha]_D^{27}$: +6.1° (c, 2.62 in H$_2$O)
* mp: 190°-192° C. (by S.D. Gero, Tetrahedron Lett. referred to hereinabove)

What is claimed is:

1. A method for the preparation of D-myoinositol-1-phosphate from a 1,2-(R$^1$)-3-R$^2$-myoinositol compound as a starting material and having the formula

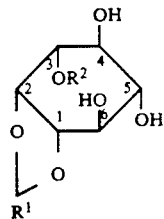

where R$^1$ is a protective group of a bridging type bonded to the two oxygen atoms at the 1- and 2-position, and R$^2$ is a protective group coupled to the oxygen atom at the 3-position, which method comprises the steps of:

(a) reacting the starting material with a benzyl or benzoyl halide to replace the hydroxyl groups at the 4-, 5- and 6-positions with a benzyl or benzoyl group, respectively;

(b) removing from compound (a) the protective group R$^1$, and the two oxygen atoms to which it is bonded at the 1- and 2-positions by reacting compound (a) with an acid to replace the substituent with two hydroxyl groups at the 1- and 2- positions;

(c) triethylsilylating compound (b) to replace the hydroxyl group at the 1-position with a triethylsilyl group;

(d) reacting compound (c) with a benzyl or benzoyl halide to replace the hydroxyl group at the 2-position with a benzyl or benzoyl group, respectively;

(e) reacting compound (d) with a Lewis acid to replace the triethylsily group at the 1-position with a hydroxyl group;

(f) reacting compound (e) with 1,5-dihydro-3-diethylamino-2,4,3-benzodioxaphosphepin, followed by oxidation to replace the hydroxyl group at the 1-position with a group of the formula:

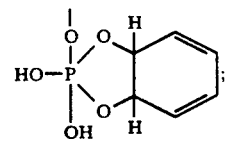

(g) reacting the compound of (f) with an alkali metal hydride to form D-myoinositol-1-phosphate.

2. The method of claim 1, in which R$_1$ is a cyclohexylidene group and R$_2$ is a benzyl or benzoyl group.

3. The method of claim 2 in which the starting material is prepared from L-quebrachitol of the formula:

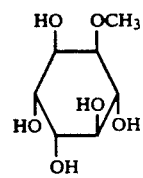

which comprises the steps of:

(a) reacting L-quebrachitol with 1-ethoxy cyclohexene to produce a compound of the formula:

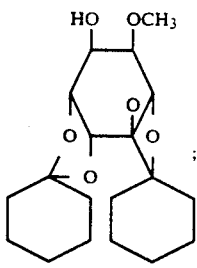

(b) oxidizing compound (a) to convert the hydroxyl group to oxygen;

(c) reducing compound (b) at −78° C. with lithium borohydride to a compound of the formula:

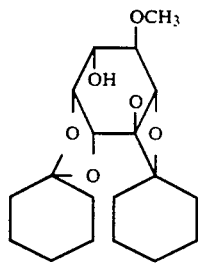

(d) reacting compound (c) with a benzyl halide or benzoyl halide to replace the hydroxyl group with a benzyl or benzoyl group respectively; and
(e) reacting compound (d) with an aluminum halide and sodium iodide to produce the starting material 1,2-(cyclohexylidene)-3-benzyl myoinositol or 1,2-(cyclohexylidene)-3-benzoyl myoinositol.

4. The method of claim 1, wherein step (a) is conducted in the presence of triethylamine as a catalyst.

5. The method of claim 1, wherein the Lewis acid in step (e) is selected from the group consisting of p-toluene sulfonate, aluminum trichloride, boron trifluoride, phosphoric acid, sulfur trioxide, zinc dichloride, tin tetrachloride and sulfuric acid.

6. The method of claim 1, wherein step (g) is effected in the presence of sodium hydride.

* * * * *